(12) United States Patent
Sato

(10) Patent No.: US 10,752,608 B2
(45) Date of Patent: Aug. 25, 2020

(54) METHOD FOR PRODUCING CRYSTAL OF URACIL COMPOUND

(71) Applicant: Sumitomo Chemical Company, Limited, Tokyo (JP)

(72) Inventor: Yuki Sato, Hyogo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/308,254

(22) PCT Filed: Jul. 13, 2017

(86) PCT No.: PCT/JP2017/025498
§ 371 (c)(1),
(2) Date: Dec. 7, 2018

(87) PCT Pub. No.: WO2018/012573
PCT Pub. Date: Jan. 18, 2018

(65) Prior Publication Data
US 2019/0263780 A1    Aug. 29, 2019

(30) Foreign Application Priority Data

Jul. 15, 2016 (JP) .................................. 2016-140053
Dec. 22, 2016 (JP) .................................. 2016-248827
Mar. 22, 2017 (JP) .................................. 2017-055556

(51) Int. Cl.
*C07D 401/12* (2006.01)
*A01N 43/54* (2006.01)

(52) U.S. Cl.
CPC ........... *C07D 401/12* (2013.01); *A01N 43/54* (2013.01); *C07B 2200/13* (2013.01)

(58) Field of Classification Search
CPC .................................................. C07D 401/12
See application file for complete search history.

(56) References Cited

U.S. PATENT DOCUMENTS

| 5,334,739 A | 8/1994 | Pastor et al. |
| 2004/0250469 A1 | 12/2004 | Baxter et al. |
| 2006/0189484 A1 | 8/2006 | Tohyama et al. |
| 2015/0321983 A1 | 11/2015 | Tois |

FOREIGN PATENT DOCUMENTS

| CN | 1316426 A | 10/2001 |
| CN | 1572839 A | 2/2005 |
| EP | 1122244 A1 | 8/2001 |
| EP | 1422227 A1 | 5/2004 |
| EP | 1486554 A1 | 12/2004 |
| JP | H08503948 A | 4/1996 |
| JP | 2002155061 A | 5/2002 |
| JP | 2003048885 A | 2/2003 |
| JP | 2003286284 A | 10/2003 |
| JP | 2003286285 A | 10/2003 |
| JP | 2003321468 A | 11/2003 |
| JP | 2005002320 A | 1/2005 |
| JP | 2015532309 A | 11/2015 |
| WO | 94012509 A1 | 6/1994 |
| WO | WO 2007/083090 A2 * | 7/2007 |
| WO | 2014060640 A1 | 4/2014 |
| WO | 2018178039 A1 | 10/2018 |

OTHER PUBLICATIONS

Asahara et al., Yozai Handbook, Kodansha Ltd. 6th print, pp. 47-51, 1985 (Partial translation).
Int'l Preliminary Report on Patentability dated Jan. 15, 2019 in Int'l Application No. PCT/JP2017/025498.
Int'l Search Report dated Aug. 15, 2017 in Int'l Application No. PCT/JP2017/025498.
Examiner Search Report dated Nov. 14, 2009 in CL 2019-00074 (with English translation).
Office Action dated Jan. 22, 2020 in CO Application No. NC2018/0012992.
Extended European Search Report dated Dec. 11, 2019 in EP Application No. 17827696.0.
Office Action dated May 26, 2020 in CN Application No. 201780040717.0.
Office Action dated Jul. 14, 2020 in JP Application No. 2017055556.

* cited by examiner

*Primary Examiner* — Emily A Bernhardt
(74) *Attorney, Agent, or Firm* — Panitch Schwarze Belisario & Nadel LLP

(57) ABSTRACT

The invention provides a method for producing a crystal of a uracil compound with high purity by a process which can be carried out in an industrial scale. Specifically, the invention provides a method for producing a crystal of a uracil compound, wherein the method comprises dissolving a composition comprising a uracil compound represented by formula (1)

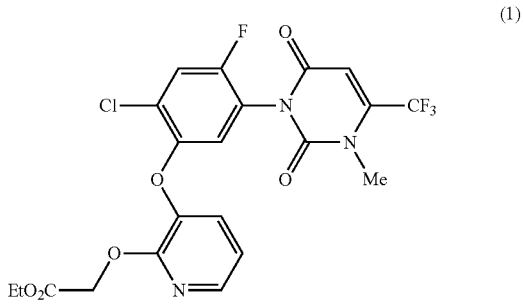

(1)

in organic solvents consisting of a C3-C6 alcohol solvent and an aromatic solvent to obtain a solution, and precipitating a crystal of said uracil compound from the solution.

5 Claims, 1 Drawing Sheet

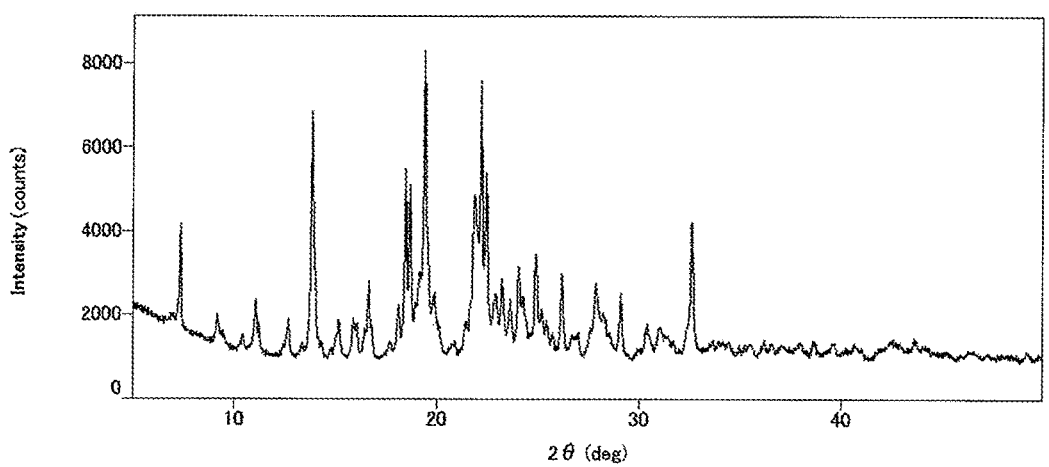

METHOD FOR PRODUCING CRYSTAL OF URACIL COMPOUND

CROSS-REFERENCE TO RELATED APPLICATION

This application is a Section 371 of International Application No. PCT/JP2017/025498, filed Jul. 13, 2017, which was published in the Japanese language on Jan. 18, 2018, under International Publication No. WO 2018/012573 A1, which claims priority under 35 U.S.C. § 119(b) to Japanese Application Nos. 2016-140053 filed on Jul. 15, 2016, 2016-248827 filed on Dec. 22, 2016, and 2017-055556 filed on Mar. 22, 2017, the disclosures of which are incorporated herein by reference in their entireties.

TECHNICAL FIELD

The present invention relates to a method for producing a crystal comprising a uracil compound which is an active ingredient of an herbicide.

BACKGROUND ART

The uracil compound represented by the following formula (1) (hereinafter referred to as "present uracil compound") is known as an active ingredient of an herbicide (Patent Literature 1; compounds 7 to 8). Further, it is described that the present uracil compound is produced by a multistep reaction process (see Patent Literatures 1 to 5 etc.)

CITATION LIST

Patent Literature

[Patent Literature 1] JP 2002-155061 A
[Patent Literature 2] JP 2003-48885 A
[Patent Literature 3] JP 2003-286284 A
[Patent Literature 4] JP 2003-286285 A
[Patent Literature 5] JP 2003-321468 A

SUMMARY OF INVENTION

Technical Problem

When an organic compound such as an agrochemical active ingredient is produced in an industrial scale by a multistep reaction process, it is important to establish a purification method to obtain a final compound with high purity.

An object of the present invention is to provide a method for producing a crystal of the present uracil compound with high purity by a process which can be carried out in an industrial scale.

Solution to Problem

The present inventors have intensively studied to find out a method for producing the present uracil compound represented by formula (1)

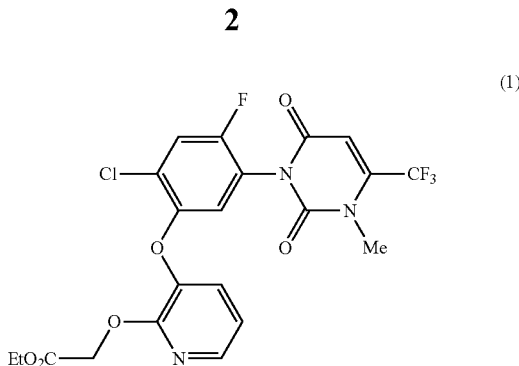

(1)

with high purity. As a result, they have found out that a crystal of the present uracil compound can be obtained with high purity by dissolving a composition comprising the present uracil compound (said composition may comprise the present uracil compound with an arbitrary purity; and hereinafter said composition is referred to as "crude uracil composition") in solvents comprising specific organic solvents, and then precipitating a crystal, to complete the present invention.

That is, a method for producing a crystal of the present uracil compound of the present invention includes the followings:

[1] A method for producing a crystal of the present uracil compound characterized in that the method comprises dissolving a crude uracil composition in organic solvents consisting of a C3-C6 alcohol solvent and an aromatic solvent to obtain a solution, and precipitating a crystal of the present uracil compound from the solution.

[2] The method for producing a crystal of the present uracil compound according to [1], wherein the crystal of the present uracil compound is precipitated by cooling a solution of a crude uracil composition.

[3] The method for producing a crystal of the present uracil compound according to [1] or [2], wherein
the C3-06 alcohol solvent is a solvent selected from the group consisting of 1-propanol, 2-propanol, 1-butanol, 2-butanol, 2-methyl-1-propanol, 2-methyl-2-propanol, 1-pentanol, 3-methyl-1-butanol, and 2-methyl-2-butanol, or a mixture of two or more of them, and
the aromatic solvent is a solvent selected from the group consisting of toluene, o-xylene, m-xylene, p-xylene, ethylbenzene, and chlorobenzene, or a mixture of two or more of them.

[4] The method for producing a crystal of the present uracil compound according to [1], [2], or [3], wherein a weight ratio of the C3-06 alcohol solvent to the aromatic solvent is 50:50 to 98:2.

Advantageous Effects of Invention

The present invention provides a method for producing a crystal of the present uracil compound with high purity, wherein the present uracil compound is the final compound produced by a multistep reaction process.

BRIEF DESCRIPTION OF DRAWINGS

A FIGURE showing an example of powder X-ray diffraction of crystals of the present uracil compound obtained by the production method of the present invention.

DESCRIPTION OF EMBODIMENTS

In the mixture consisting of two types of organic solvent used in the present invention, one solvent is a C3-C6 alcohol solvent (hereinafter referred to as "Solvent A"), and the other solvent is an aromatic solvent (hereinafter referred to as "Solvent B").

Solvent A is a solvent represented by formula ROH (wherein R is a C3-C6 hydrocarbon group), and specific examples of Solvent A include alcohol solvents such as 1-propanol, 2-propanol (isopropyl alcohol), 1-butanol, 2-butanol (sec-butyl alcohol), 2-methyl-1-propanol (isobutyl alcohol), 2-methyl-2-propanol (tert-butyl alcohol), 1-pentanol, 3-methyl-1-butanol (isoamyl alcohol), 2-methyl-2-butanol (tert-amyl alcohol), 1-hexanol, and cyclohexanol.

Solvent B is a solvent which is benzene optionally substituted with one or more halogen atoms (for example, chlorine atoms) or one or more C1-C3 aliphatic hydrocarbon groups optionally substituted with said one or more halogen atoms, and preferably benzene optionally substituted with one or more C1-C3 aliphatic hydrocarbon groups or one or more chlorine atoms, and specific examples of Solvent B include aromatic solvents such as benzene, toluene, o-xylene, m-xylene, p-xylene, ethylbenzene, propylbenzene, isopropylbenzene, 1,3,5-trimethylbenzene (mesitylene), 1,2,4-trimethylbenzene (pseudocumene), chlorobenzene, o-dichlorobenzene, m-dichlorobenzene, and p-dichlorobenzene.

The present uracil compound used in the production method of the present invention can be produced by, for example, any one of the following scheme (2) to scheme (5).

Scheme (2)

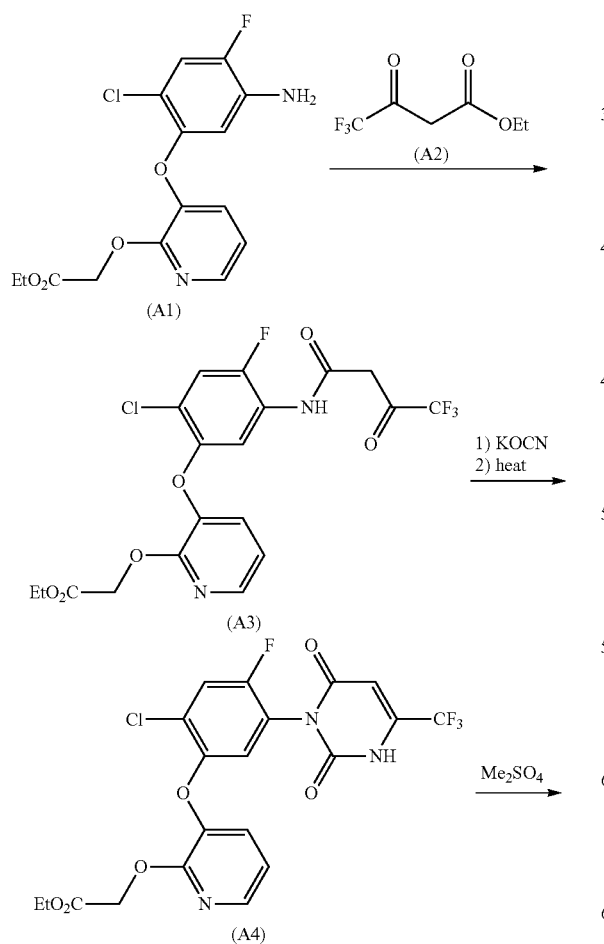

Scheme (3)

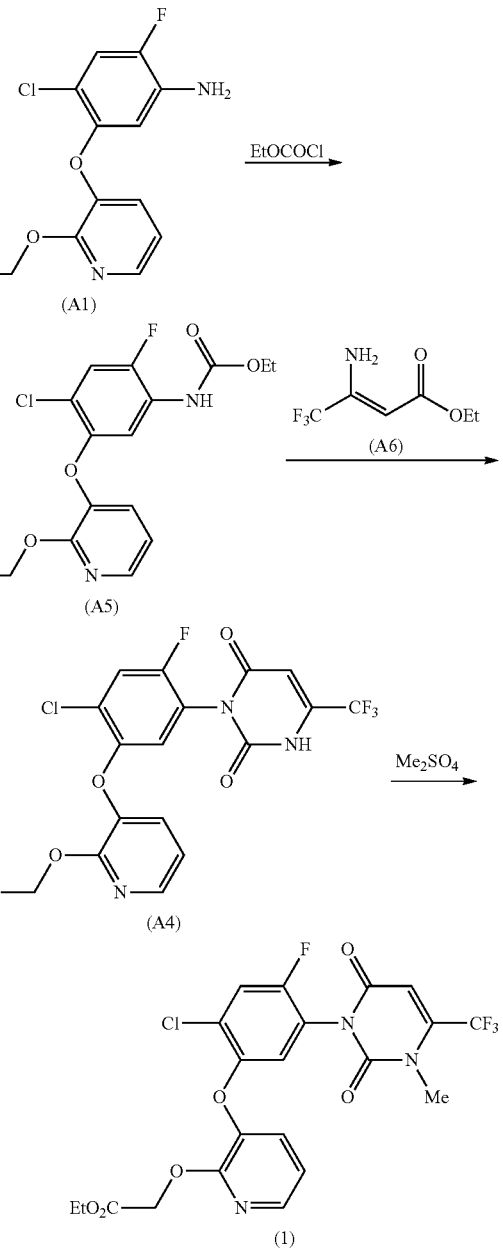

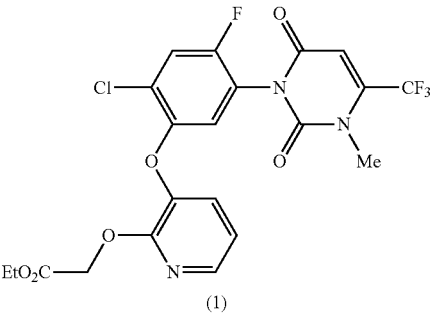

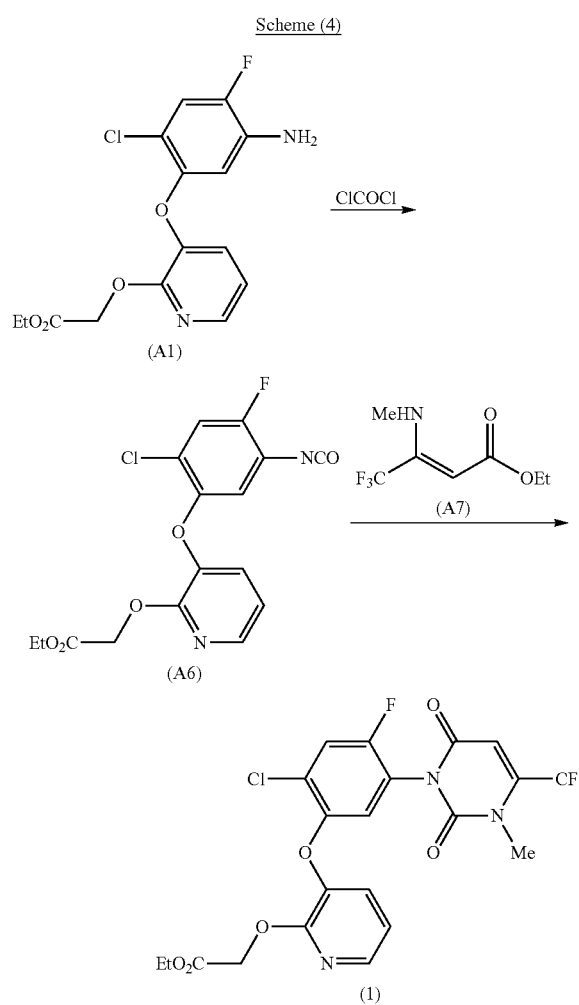

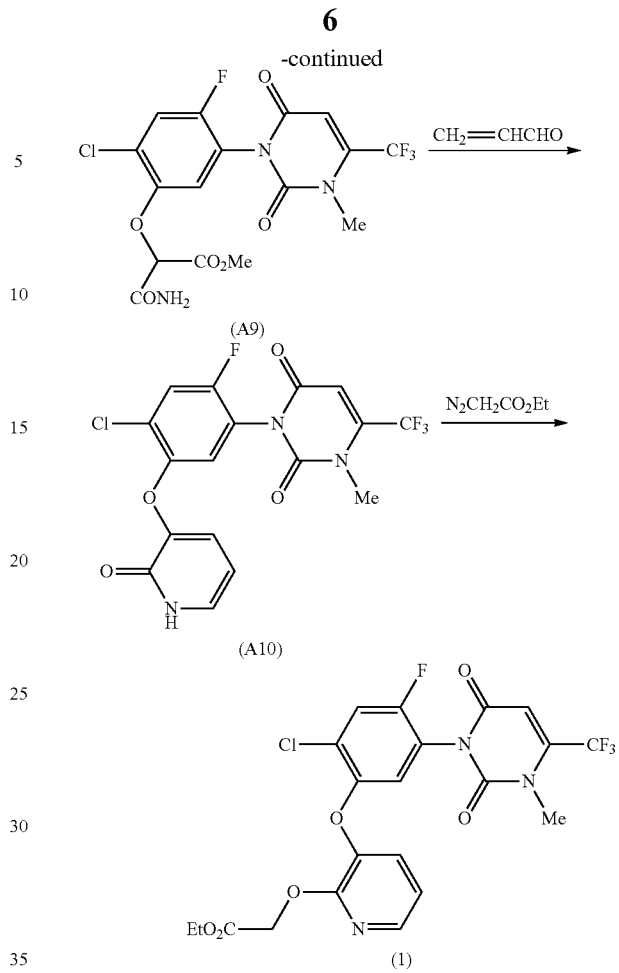

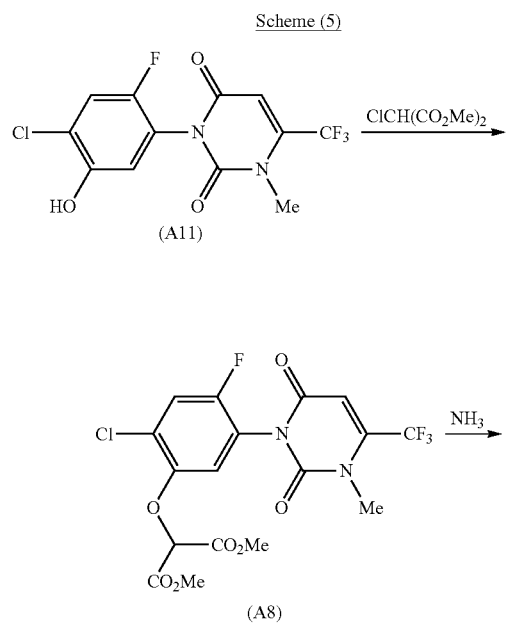

In the scheme (2) to scheme (5), the compound represented by formula (A1) (hereinafter referred to as "Compound (A1)") and the compound represented by formula (A11) (hereinafter referred to as "Compound (A11)") are described in JP 2002-363170 A or WO 2007/083090 pamphlet etc., and can be produced by a method described in said literatures.

The crude uracil composition comprises 60 to 97% by weight of the present uracil compound, and also comprises a compound such as a production intermediate in the scheme (2) to scheme (5) and a derivative derived from said production intermediate etc. (hereinafter referred to as "present contaminating compound") or tar component.

Specific examples of the present contaminating compound include a production intermediate which is solid at room temperature such as the Compound (A1), the compound represented by formula (A3) (hereinafter referred to as "Compound (A3)"), the compound represented by formula (A4) (hereinafter referred to as "Compound (A4)"), the compound represented by formula (A5) (hereinafter referred to as "Compound (A5)"), the compound represented by formula (A8) (hereinafter referred to as "Compound (A8)"), the compound represented by formula (A9) (hereinafter referred to as "Compound (A9)"), the compound represented by formula (A10) (hereinafter referred to as "Compound (A10)"), and the Compound (A11) in the scheme (2) to scheme (5), and a derivative derived from said production intermediate.

In the present invention, the ratio of the crude uracil composition to the organic solvents (Solvent A and Solvent B) is based on the content of the pure present uracil compound in the crude uracil composition. In the production method of the present invention, the (total) amount of the solvents at the time of crystal precipitation of the present uracil compound is 1.5 to 20 parts by weight, for example 2 to 20 parts by weight per one part by weight of the pure present uracil compound.

As the methods for precipitating a crystal of the present uracil compound from a solution of the crude uracil composition in the present invention, "crystallization by cooling" which comprises cooling said solution or "crystallization by poor solvent addition" which comprises gradually adding a solvent in which the present uracil compound is poorly dissolved can be used. In both methods, a crystal of the present uracil compound precipitates at a temperature within the range of −10 to 80° C., and preferably −10 to 50° C.

Solvent A and Solvent B may be each one solvent selected from each group, or a mixed solvent of two or more solvents selected from each group. When the crude uracil composition is dissolved in organic solvents, the crude uracil composition may be added to a mixture of Solvent A and Solvent B, or the crude uracil composition may be dissolved in Solvent A and then Solvent B may be added thereto.

The ratio of Solvent A to Solvent B is SolventA:Solvent B=10:90 to 99:1, preferably 50:50 to 98:2, and more preferably 60:40 to 98:2 by weight ratio at the time when the present uracil compound precipitates.

The present uracil compound precipitated from solvents is filtrated or washed by a conventional method to separate it from a mother liquor as a wet cake. Said wet cake may be dried by a conventional method such as through-flow drying using an inert gas such as nitrogen and helium, heat drying, reduced-pressure drying, and a combined drying method thereof.

Examples of preferable embodiments of the present invention include the following embodiments.

As Solvent A, a solvent selected from the group consisting of 1-propanol, 2-propanol, 1-butanol, 2-butanol, 2-methyl-1-propanol, 2-methyl-2-propanol, 1-pentanol, 3-methyl-1-butanol, and 2-methyl-2-butanol, or a mixture of two or more of them is preferable. 2-Propanol is especially preferable.

As Solvent B, a solvent selected from the group consisting of toluene, o-xylene, m-xylene, p-xylene, ethylbenzene, and chlorobenzene, or a mixture of two or more of them is preferable. A solvent selected from the group consisting of o-xylene, m-xylene, p-xylene, and ethylbenzene, or a mixture of two or more of them is especially preferable.

When Solvent A is 2-propanol, the ratio of Solvent A to Solvent B is preferably in the range of 2-propanol:Solvent B=80:20 to 98:2, and more preferably in the range of 85:15 to 98:2 by weight ratio.

The preferable range of total amount of Solvent A and Solvent B varies depending on the content of the present uracil compound in the crude uracil composition, and usually 2 to 8 parts by weight is preferable, and 3 to 8 parts by weight is more preferable per one part by weight of the pure present uracil compound in the crude uracil composition.

The method for producing the crude uracil composition in the present invention is not limited. Specific examples of the crude uracil composition include the crude uracil composition produced according to the method described in the above scheme (2).

The present invention also includes the following method for producing a crystal of the present uracil compound.

A method for producing a crystal of the present uracil compound, the method comprising (Step 1) reacting the Compound (A1)

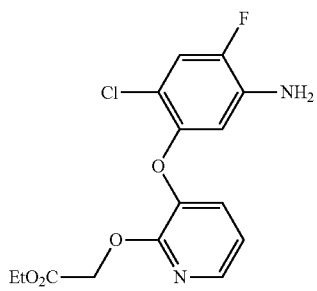

(A1)

with an alkyl trifluoroacetoacetate;

(Step 2) reacting a crude product comprising the Compound (A3) obtained in Step 1

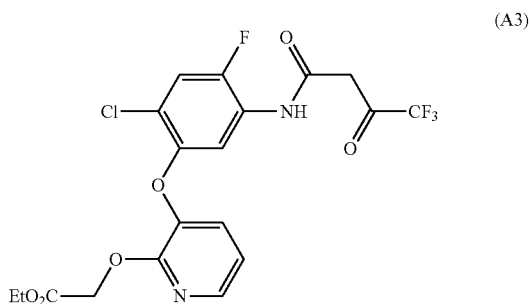

(A3)

with a cyanate in the presence of a protonic acid;

(Step 3) reacting a crude product comprising the Compound (A4) obtained in Step 2

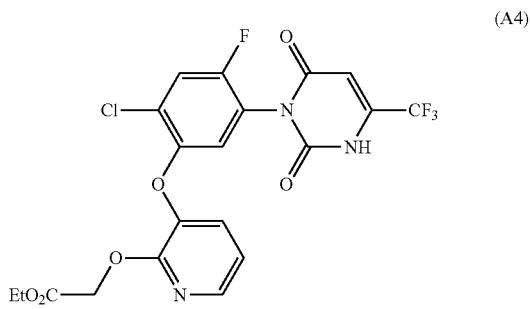 [SMILES: CCOC(=O)COc1ncccc1Oc1cc(-n2c(=O)cc(C(F)(F)F)[nH]c2=O)c(F)cc1Cl]

(A4)

with a methylating agent in the presence of a base; and (Step 4) dissolving a crude product comprising the present uracil compound obtained in Step 3 in organic solvents consisting of a C3-C6 alcohol solvent and an aromatic solvent to obtain a solution, and precipitating a crystal of the present uracil compound from the solution.

Examples of the alkyl trifluoroacetoacetate in Step 1 include ethyl 4,4,4-trifluoroacetoacetate and methyl 4,4,4-trifluoroacetoacetate.

Examples of the cyanate in Step 2 include potassium cyanate and sodium cyanate. Examples of the protonic acid include organic acids (for example, acetic acid, propionic acid, butyric acid, benzoic acid, p-toluenesulfonic acid, and methanesulfonic acid), and inorganic acids (for example, hydrochloric acid and sulfuric acid).

Examples of the methylating agent in Step 3 include methyl iodide, methyl bromide, and dimethyl sulfate. Examples of the base include triethylamine, diisopropylethylamine, potassium carbonate, and sodium carbonate.

An example of measurement result of powder X-ray diffraction of crystals of the present uracil compound obtained by the production method of the present invention is shown in FIG. 1. In one embodiment, the crystals of the present uracil compound have diffraction peaks as shown in Table 1 in powder X-ray diffraction using Cu-Kα radiation.

TABLE 1

| 2θ value (deg) | d value (Å) | Relative height (%) |
|---|---|---|
| 7.4 | 11.96 | 32.1 |
| 13.8 | 6.41 | 72.5 |
| 17.7 | 5.01 | 100.0 |
| 18.5 | 4.80 | 52.2 |
| 18.7 | 4.75 | 43.9 |
| 19.4 | 4.57 | 73.8 |
| 21.8 | 4.07 | 42.1 |
| 22.2 | 4.00 | 70.5 |
| 22.5 | 3.96 | 46.8 |
| 24.0 | 3.70 | 24.1 |
| 24.9 | 3.58 | 28.5 |
| 26.2 | 3.40 | 23.0 |
| 32.6 | 2.75 | 48.4 |

Namely, in one embodiment, crystals of the present uracil compound are crystals having diffraction peaks mainly at 2θ=7.4±0.2°, 13.8±0.2°, 17.7±0.2°, 18.5±0.2°, 18.7±0.2°, 19.4±0.2°, 21.8±0.2°, 22.2±0.2°, 22.5±0.2°, 24.0±0.2°, 24.9±0.2°, 26.2±0.2°, and 32.6±0.2° in powder X-ray diffraction using Cu-Kα radiation.

The conditions for the powder X-ray diffraction are as follows.
(Measurement Conditions)
Device for powder X-ray diffraction: SmartLab (manufactured by Rigaku Corporation)
X-ray output: CuKα, 45 kV, 200 mA
Sampling interval: 0.02°
Scan range: 5° to 50°

EXAMPLES

Hereinafter, the present invention is described in detail by Examples.

Unless otherwise specified, the content in Examples was determined by absolute calibration curve method using high performance liquid chromatography.

Reference Preparation Example 1

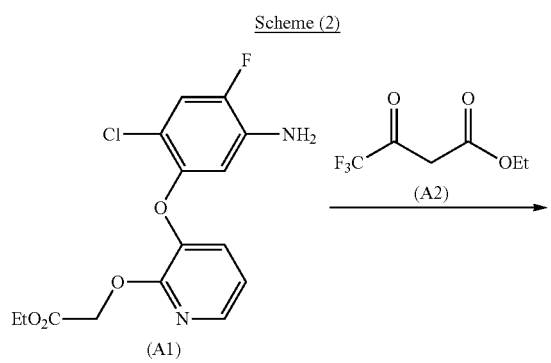

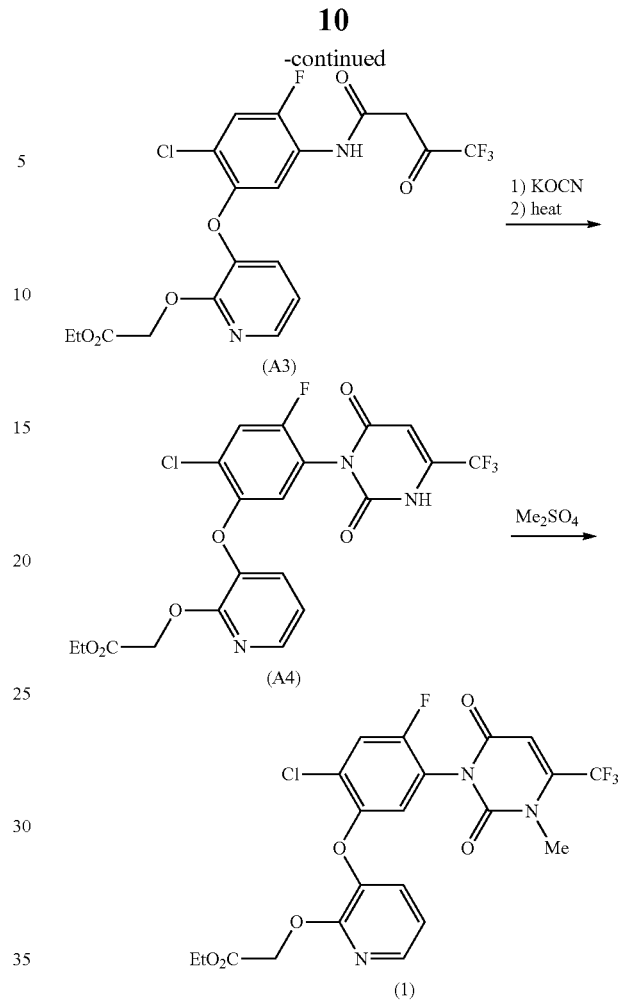

The crude uracil composition was prepared by the production route in scheme (2). A purification step such as silica gel column chromatography was not carried out also in the first step and the second step, and the crude product obtained in each step was used as a stating material in the next step.

Example 1

To a flask were added 126.6 parts by weight of a composition comprising the present uracil compound obtained in Reference Preparation Example 1 (content of the present uracil compound: 79.0%; comprising 100 parts by weight of the pure present uracil compound), 316.5 parts by weight of 2-propanol (manufactured by Kanto Chemical Co., Inc.), and 64.6 parts by weight of xylene (manufactured by Sumitomo Shoji Chemicals Co., Ltd.; a mixture of o-xylene, m-xylene, p-xylene, and ethylbenzene), and the resulting mixture was heated to 70° C. under nitrogen atmosphere. Upon confirmation that there was no insoluble matter, said mixture was gradually cooled with stirring, and then crystal precipitation was initiated at 35° C. After the mixture was further cooled to 0° C., the resulting crystals were separated by filtration. Said crystals were washed with 253.2 parts by weight of a cooled mixed solvent of 2-propanol (the same as above) and xylene (the same as above) with a mixture ratio of 5:1 (by weight ratio). After washing, the crystals were dried under reduced pressure to obtain 74.7 parts by weight of the crystals of the present uracil compound.

The content of the present uracil compound in the resulting crystals of the present uracil compound was 96.4%.

The results of analysis of the composition before crystallization and the resulting crystals by high performance liquid chromatography are shown below.

It could be confirmed that the resulting crystals comprised the present uracil compound with high purity, and the reduced contents of Compound (A1) and Compound (A3).

TABLE 2

| Area percentage | Composition before crystallization | Resulting crystals |
|---|---|---|
| Present uracil compound | 85.6% | 97.6% |
| Compound (A3) | 0.9% | 0.1% |
| Compound (A1) | 1.1% | 0.2% |

*Measurement conditions of liquid chromatography

Device: Shimadzu LC-20A, HPLC,

Column: SUMIPAX ODS Z-CLUE (3 μm 4.6 mmΦ×100 mm),

Mobile phase: Solution A: 0.1% phosphoric acid aqueous solution,

Solution B: acetonitrile,

Ratio of Solution B: 10% (0 min)–[30 min]→90% (5 min)→10% (15 min),

Flow rate: 1 mL/min, Temperature: 40° C., Detection wavelength: 274 nm

The following analogous compounds of the present uracil compound or production intermediates thereof are added to the crude uracil composition, and the composition is subjected to the production method of the present invention to confirm that the production method of the present invention has excellent purification effects also on the compounds other than Compound (A1) and Compound (A3).

Example 2

A mixture of the crude uracil composition (comprising 100 parts by weight of the pure present uracil compound) comprising 0.1 to 1% of each compound prepared in the following Reference Preparation Examples 2 to 8, 300 parts by weight of 2-propanol, and 65 parts by weight of xylene is heated to 70° C. Said mixture is gradually cooled to initiate crystal precipitation at a temperature of 50° C. or less. After the mixture is further cooled to 0° C., the resulting crystals are separated by filtration. The crystals are washed with a mixed solvent of 2-propanol and xylene with a mixture ratio of 5:1 (by weight ratio). After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

The methods for producing the compounds added to the crude uracil composition described in Example 2 are shown below.

Reference Preparation Example 2

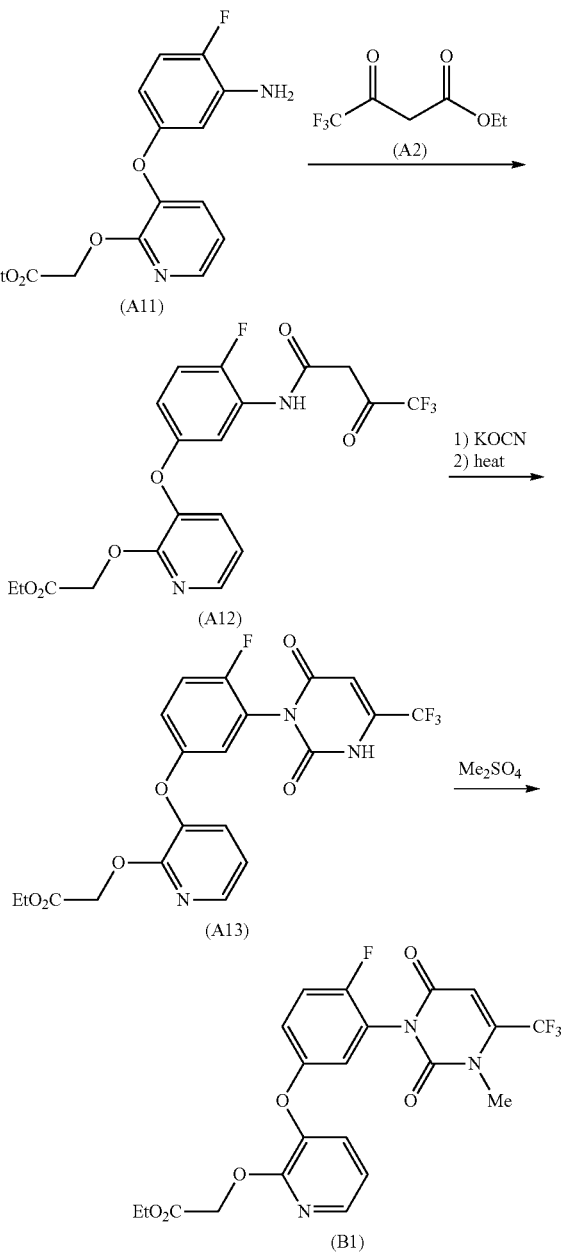

The Compound (A11) (1.0 mmol) and ethyl 4,4,4-trifluoroacetoacetate (1.0 mmol) were dissolved in toluene 10 ml, and said mixture was heated under reflux with stirring for 3 hours. The reflux solution was passed through a column filled with molecular sieves 5 A to adsorb ethanol. The reaction solution was cooled to obtain the compound represented by formula (A12) (hereinafter referred to as "Compound (A12)").

To a mixture of the Compound (A12) (0.8 mmol) and acetic acid 3 ml was added potassium cyanate (0.8 mmol), and the mixture was stirred at 50° C. for one hour, and additionally stirred at 110° C. for 2 hours. The reaction mixture was cooled, then poured into water, and extracted with ethyl acetate. The organic layers were washed with saturated brine and concentrated, and the residues were subjected to column chromatography to obtain the compound represented by formula (A13) (hereinafter referred to as "Compound (A13)").

To a mixture of the Compound (A13) (0.5 mmol), potassium carbonate (0.7 mmol), and acetonitrile 5 ml was added dimethyl sulfate (0.7 mmol) at room temperature, and the mixture was stirred at 50° C. for one hour. The reaction mixture was cooled, then poured into water, and extracted with toluene. The organic layers were washed with saturated brine and concentrated, and the residues were subjected to column chromatography to obtain the compound represented by formula (B1) (hereinafter referred to as "Compound (B1)").

The physical properties of the Compound (B1) are shown below.

$^1$H-NMR (CD$_3$CN-D$_2$O) δ: 7.93 (1H, dd, J=4.9, 1.5 Hz), 7.45 (1H, dd, J=7.6, 1.5 Hz), 7.26-7.24 (1H, m), 7.07-7.06 (1H, m), 7.03-7.02 (1H, m), 6.93-6.92 (1H, m), 6.33 (1H, s), 4.85-4.84 (2H, m), 4.14 (2H, q, J=7.1 Hz), 3.43 (3H, s), 1.19 (3H, t, J=7.1 Hz).

Reference Preparation Example 3

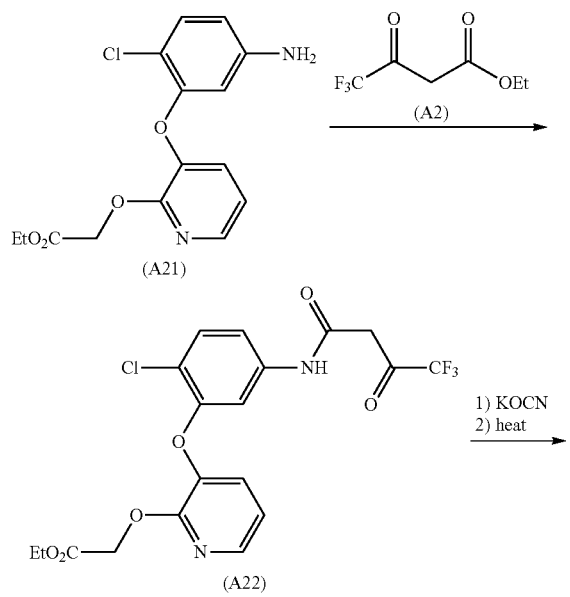

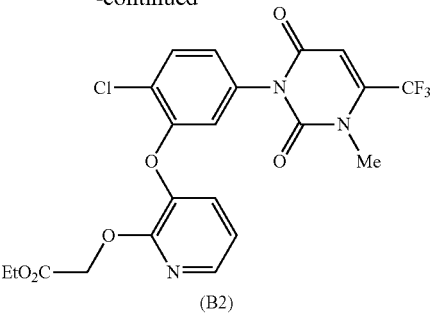

The compound represented by formula (A21) (hereinafter referred to as "Compound (A21)") (1.0 mmol) and ethyl 4,4,4-trifluoroacetoacetate (1.0 mmol) are dissolved in toluene 10 ml, and said mixture is heated under reflux with stirring for 3 hours. The reflux solution is passed through a column filled with molecular sieves 5 A to adsorb ethanol. The reaction solution is cooled to obtain the compound represented by formula (A22) (hereinafter referred to as "Compound (A22)").

To a mixture of the Compound (A22) (0.8 mmol) and acetic acid 3 ml is added potassium cyanate (0.8 mmol), and the mixture is stirred at 50° C. for one hour, and additionally stirred at 110° C. for 2 hours. The reaction mixture is cooled, then poured into water, and extracted with ethyl acetate. The organic layers are washed with saturated brine and concentrated, and the residues are subjected to column chromatography to obtain the compound represented by formula (A23) (hereinafter referred to as "Compound (A23)").

To a mixture of the Compound (A23) (0.5 mmol), potassium carbonate (0.7 mmol), and acetonitrile 5 ml is added dimethyl sulfate (0.7 mmol) at room temperature, and the mixture is stirred at 50° C. for one hour. The reaction mixture is cooled, then poured into water, and extracted with toluene. The organic layers are washed with saturated brine and concentrated, and the residues are subjected to column chromatography to obtain the compound represented by formula (B2) (hereinafter referred to as "Compound (B2)").

Reference Preparation Example 4

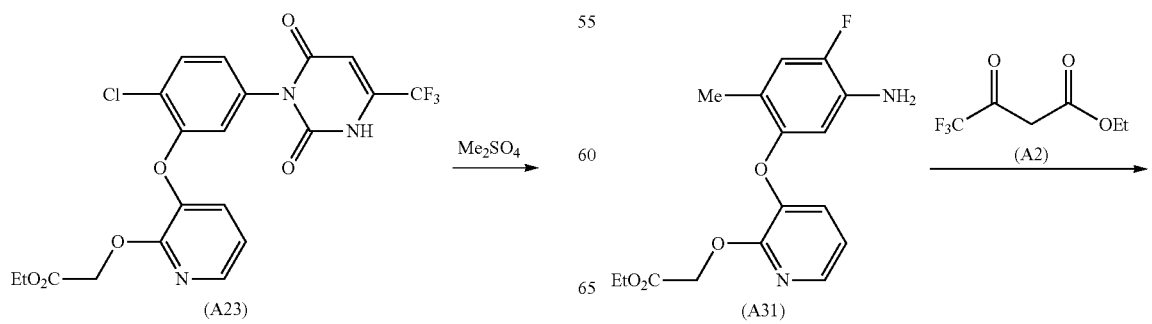

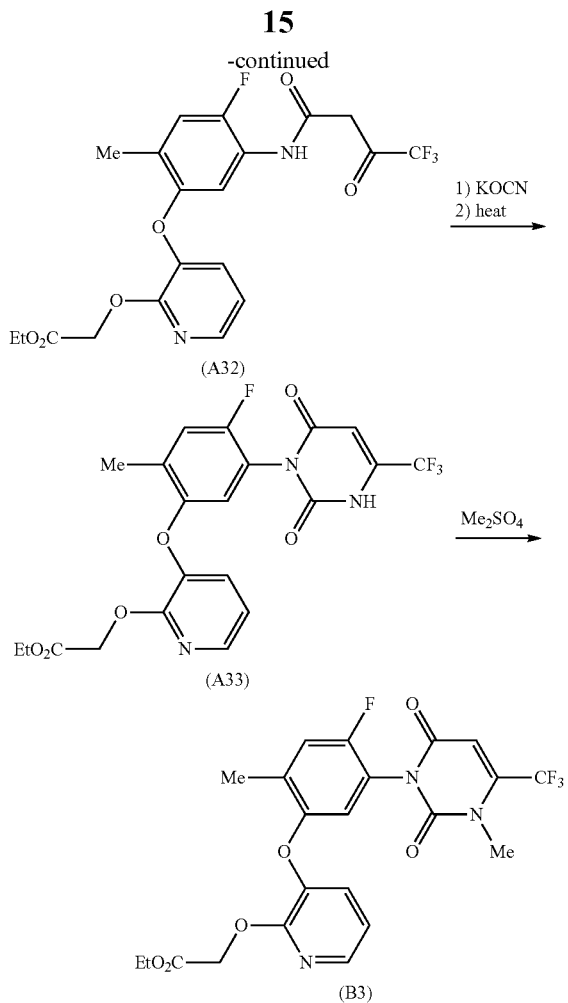

(A32)

(A33)

(B3)

Reference Preparation Example 5

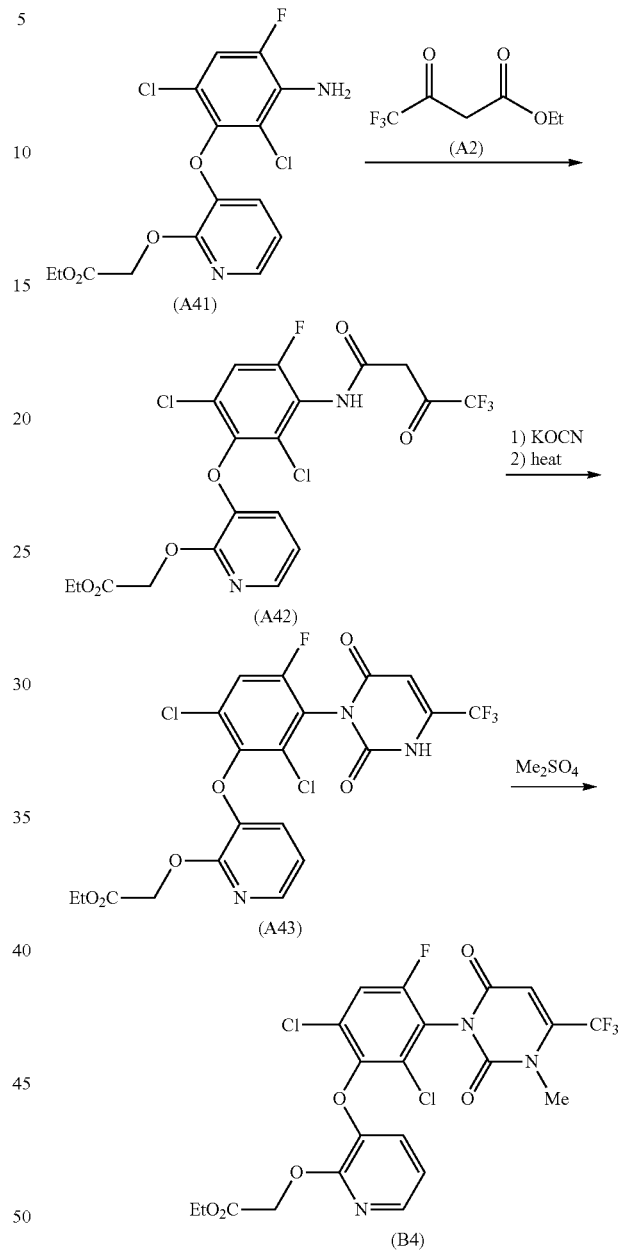

(A41)

(A42)

(A43)

(B4)

The compound represented by formula (A31) (hereinafter referred to as "Compound (A31)") (1.0 mmol) and ethyl 4,4,4-trifluoroacetoacetate (1.0 mmol) are dissolved in toluene 10 ml, and said mixture is heated under reflux with stirring for 3 hours. The reflux solution is passed through a column filled with molecular sieves 5 A to adsorb ethanol. The reaction solution is cooled to obtain the compound represented by formula (A32) (hereinafter referred to as "Compound (A32)")

To a mixture of the Compound (A32) (0.8 mmol) and acetic acid 3 ml is added potassium cyanate (0.8 mmol), and the mixture is stirred at 50° C. for one hour, and additionally stirred at 110° C. for 2 hours. The reaction mixture is cooled, then poured into water, and extracted with ethyl acetate. The organic layers are washed with saturated brine and concentrated, and the residues are subjected to column chromatography to obtain the compound represented by formula (A33) (hereinafter referred to as "Compound (A33)").

To a mixture of the Compound (A33) (0.5 mmol), potassium carbonate (0.7 mmol), and acetonitrile 5 ml is added dimethyl sulfate (0.7 mmol) at room temperature, and the mixture is stirred at 50° C. for one hour. The reaction mixture is cooled, then poured into water, and extracted with toluene. The organic layers are washed with saturated brine and concentrated, and the residues are subjected to column chromatography to obtain the compound represented by formula (B3) (hereinafter referred to as "Compound (B3)").

The compound represented by formula (A41) (hereinafter referred to as "Compound (A41)") (1.0 mmol) and ethyl 4,4,4-trifluoroacetoacetate (1.0 mmol) are dissolved in toluene 10 ml, and said mixture is heated under reflux with stirring for 3 hours. The reflux solution is passed through a column filled with molecular sieves 5 A to adsorb ethanol. The reaction solution is cooled to obtain the compound represented by formula (A42) (hereinafter referred to as "Compound (A42)").

To a mixture of the Compound (A42) (0.8 mmol) and acetic acid 3 ml is added potassium cyanate (0.8 mmol), and the mixture is stirred at 50° C. for one hour, and additionally stirred at 110° C. for 2 hours. The reaction mixture is cooled, then poured into water, and extracted with ethyl acetate. The organic layers are washed with saturated brine and concentrated, and the residues are subjected to column chromatography to obtain the compound represented by formula (A43) (hereinafter referred to as "Compound (A43)").

To a mixture of the Compound (A43) (0.5 mmol), potassium carbonate (0.7 mmol), and acetonitrile 5 ml is added dimethyl sulfate (0.7 mmol) at room temperature, and the mixture is stirred at 50° C. for one hour. The reaction mixture is cooled, then poured into water, and extracted with toluene. The organic layers are washed with saturated brine and concentrated, and the residues are subjected to column chromatography to obtain the compound represented by formula (B4) (hereinafter referred to as "Compound (B4)").

Reference Preparation Example 6

Reference Preparation Example 7

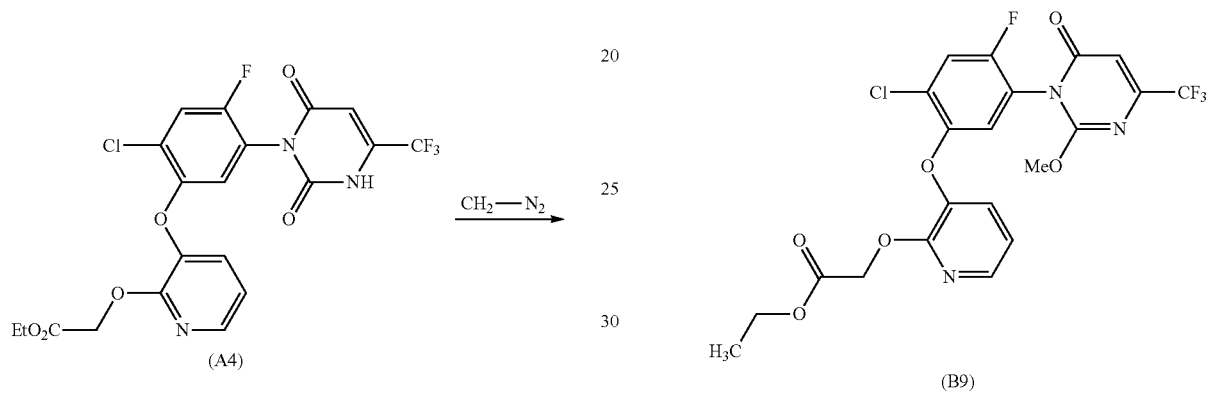

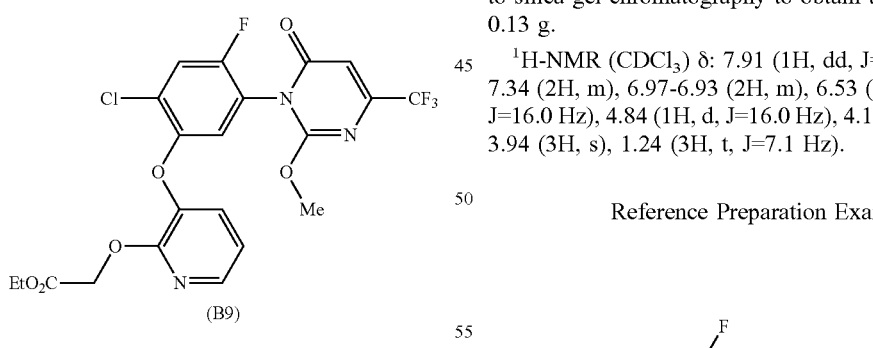

The Compound (A4) (1.0 mmol) was dissolved in toluene 5 ml, and to the mixture was added dropwise a solution of diazomethane (1.0 mmol) in toluene 1 ml at room temperature. Then, the reaction solution was poured into water, and extracted with toluene. The organic layers were washed with saturated brine and concentrated. The residues were subjected to silica gel chromatography to obtain the compound represented by formula (59) (hereinafter referred to as "Compound (B9)").

LC/MS (ESI-MS(posi)): 518[M+H]$^+$

To a mixture of the Compound (A4) 0.71 g, toluene 50 mL, and methanol 10 mL was added dropwise a solution of trimethylsilyldiazomethane in hexane (0.6 mol/L) 4.7 mL under ice-cooling. The mixture was stirred at the same temperature for 30 minutes, and then acetic acid was added thereto until bubbling stopped. The reaction mixture was concentrated, and then the resulting residues were subjected to silica gel chromatography to obtain the Compound (B9) 0.13 g.

$^1$H-NMR (CDCl$_3$) δ: 7.91 (1H, dd, J=5.0, 1.6 Hz), 7.39-7.34 (2H, m), 6.97-6.93 (2H, m), 6.53 (1H, s), 5.02 (1H, d, J=16.0 Hz), 4.84 (1H, d, J=16.0 Hz), 4.15 (2H, q, J=7.1 Hz), 3.94 (3H, s), 1.24 (3H, t, J=7.1 Hz).

Reference Preparation Example 8

-continued

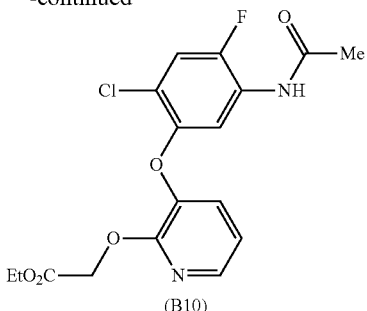

(B10)

The Compound (A1) (1.0 mmol) and triethylamine (1.5 mmol) were dissolved in tetrahydrofuran 8 ml, and acetyl chloride (1.5 mmol) was added thereto at room temperature. Said mixture was stirred at 40° C., and then the reaction solution was poured into water. The resulting mixture was extracted with ethyl acetate, and the organic layers were washed with saturated brine and concentrated. The resulting residues were subjected to column chromatography to obtain the compound represented by formula (B10) (hereinafter referred to as "Compound (B10)")

LC/MS (ESI-MS (posi)): 383 [M+H]$^+$

Example 3

A mixture of the crude uracil composition (comprising 100 parts by weight of the pure present uracil compound) comprising 0.1 to 1% of each compound prepared in the above Reference Preparation Examples 2 to 8, 169 parts by weight of 2-propanol, and 4 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with 2-propanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Example 4

A mixture of the crude uracil composition (comprising 100 parts by weight of the pure present uracil compound) comprising 0.1 to 1% of each compound prepared in the above Reference Preparation Examples 2 to 8, 160 parts by weight of 2-propanol, and 18 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with 2-propanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Example 5

A mixture of the crude uracil composition (comprising 100 parts by weight of the pure present uracil compound) comprising 0.1 to 1% of each compound prepared in the above Reference Preparation Examples 2 to 8, 255 parts by weight of 2-propanol, and 28 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with 2-propanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Example 6

A mixture of the crude uracil composition (comprising 100 parts by weight of the pure present uracil compound) comprising 0.1 to 1% of each compound prepared in the above Reference Preparation Examples 2 to 8, 141 parts by weight of 2-propanol, and 36 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with 2-propanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Example 7

A mixture of the crude uracil composition (comprising 100 parts by weight of the pure present uracil compound) comprising 0.1 to 1% of each compound prepared in the above Reference Preparation Examples 2 to 8, 256 parts by weight of 2-propanol, and 29 parts by weight of toluene is heated to 60° C. Said mixture is gradually cooled to initiate crystal precipitation at a temperature of 50° C. or less. After the mixture is further cooled to 0° C., the resulting crystals are separated by filtration. The crystals are washed with 2-propanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Example 8

A mixture of the crude uracil composition (comprising 100 parts by weight of the pure present uracil compound) comprising 0.1 to 1% of each compound prepared in the above Reference Preparation Examples 2 to 8, 255 parts by weight of 1-butanol, and 27 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with 1-butanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Example 9

A mixture of the crude uracil composition (comprising 100 parts by weight of the pure present uracil compound) comprising 0.1 to 1% of each compound prepared in the above Reference Preparation Examples 2 to 8, 255 parts by weight of 2-propanol, and 29 parts by weight of chlorobenzene is heated to 60° C. Said mixture is gradually cooled to initiate crystal precipitation at a temperature of 50° C. or less. After the mixture is further cooled to 0° C., the resulting crystals are separated by filtration. The crystals are washed with 2-propanol of 0° C. After washing, the crystals are dried under reduced pressure to obtain the crystals of the present uracil compounds.

The resulting crystals are analyzed to confirm that they comprise the present uracil compound with high purity, and the reduced contents of compounds other than the present uracil compound.

Comparative Example 1

A mixture of the crude uracil composition (comprising 100 parts by weight of the pure present uracil compound) comprising 0.1 to 1% of each compound prepared in the above Reference Preparation Examples 2 to 8, 271 parts by weight of ethanol, and 11 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with ethanol of 0° C. After washing, the crystals are dried under reduced pressure to obtain the crystals of the present uracil compounds.

Comparative Example 2

A mixture of the crude uracil composition (comprising 100 parts by weight of the pure present uracil compound) comprising 0.1 to 1% of each compound prepared in the above Reference Preparation Examples 2 to 8, 281 parts by weight of ethanol, and 2 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with ethanol of 0° C. After washing, the crystals are dried under reduced pressure to obtain the crystals of the present uracil compounds.

Comparative Example 3

A mixture of the crude uracil composition (comprising 100 parts by weight of the pure present uracil compound) comprising 0.1 to 1% of each compound prepared in the above Reference Preparation Examples 2 to 8, 270 parts by weight of methanol, and 10 parts by weight of xylene is heated to 60° C. Said mixture is gradually cooled to initiate crystal precipitation at a temperature of 50° C. or less. After the mixture is further cooled to 0° C., the resulting crystals are separated by filtration. The crystals are washed with methanol of 0° C. After washing, the crystals are dried under reduced pressure to obtain the crystals of the present uracil compounds.

INDUSTRIAL APPLICABILITY

A crystal of the present uracil compound with high purity can be obtained by the production method of the present invention.

The invention claimed is:

1. A method for producing a crystalline uracil compound represented by formula (1)

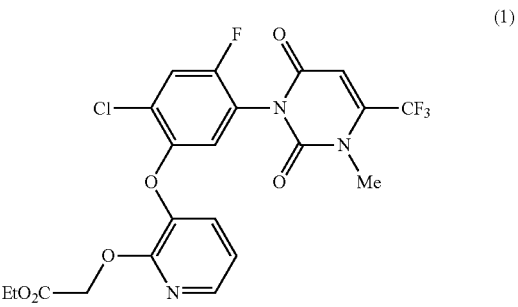 [SMILES: CCOC(=O)COc1ncccc1Oc1cc(-n2c(=O)cc(C(F)(F)F)n(C)c2=O)c(F)cc1Cl]

wherein the method comprises dissolving a composition comprising the uracil compound in organic solvents consisting of a C3-C6 alcohol solvent and an aromatic solvent to obtain a solution, and precipitating the crystalline uracil compound from the solution.

2. The method for producing the crystalline uracil compound according to claim 1, wherein the crystalline uracil compound is precipitated by cooling a solution of a crude composition.

3. The method for producing the crystalline uracil compound according to claim 1, wherein
the C3-C6 alcohol solvent is a solvent selected from the group consisting of 1-propanol, 2-propanol, 1-butanol, 2-butanol, 2-methyl-1-propanol, 2-methyl-2-propanol, 1-pentanol, 3-methyl-1-butanol, and 2-methyl-2-butanol, or a mixture of two or more of them, and
the aromatic solvent is a solvent selected from the group consisting of toluene, o-xylene, m-xylene, p-xylene, ethylbenzene, and chlorobenzene, or a mixture of two or more of them.

4. The method for producing the crystalline uracil compound according to claim 1, wherein a weight ratio of the C3-C6 alcohol solvent to the aromatic solvent is 50:50 to 98:2.

5. A method for producing a crystalline uracil compound represented by formula (1)

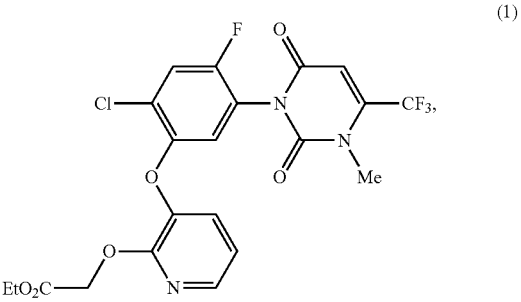 [SMILES: CCOC(=O)COc1ncccc1Oc1cc(-n2c(=O)cc(C(F)(F)F)n(C)c2=O)c(F)cc1Cl]

the method comprising

Step 1: reacting a compound represented by formula (A1)

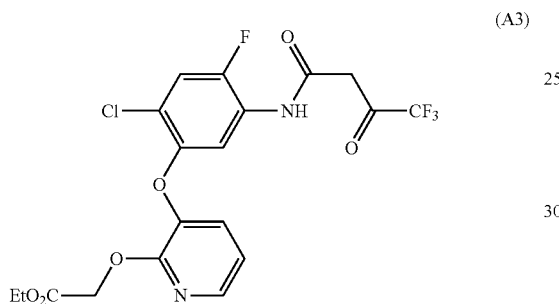
(A1)

with an alkyl trifluoroacetoacetate;

Step 2: reacting a crude product comprising a compound represented by formula (A3) obtained in Step 1

(A3)

with a cyanate in the presence of a protonic acid;

Step 3: reacting a crude product comprising a compound represented by formula (A4) obtained in Step 2

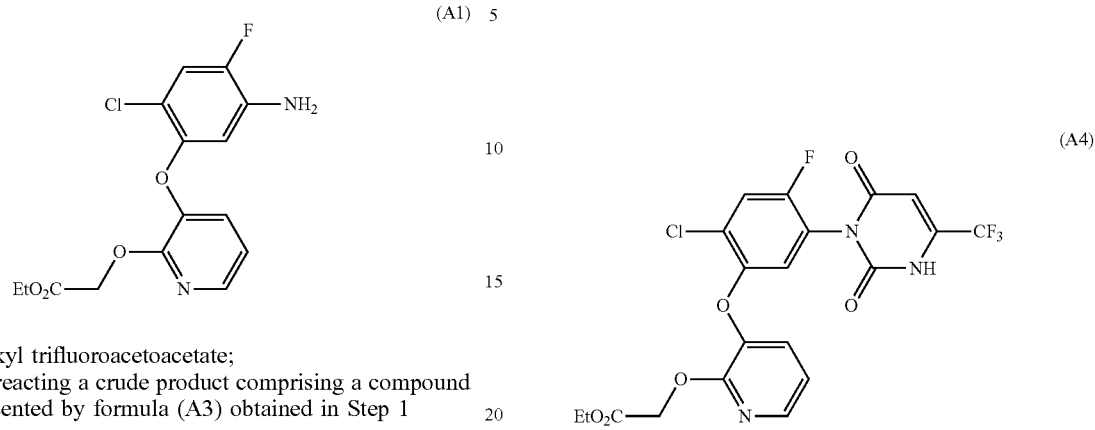
(A4)

with a methylating agent in the presence of a base; and

Step 4: dissolving a crude product comprising the uracil compound represented by formula (1) obtained in Step 3 in organic solvents consisting of a C3-C6 alcohol solvent and an aromatic solvent to obtain a solution, and precipitating the crystalline uracil compound from the solution.

* * * * *